United States Patent [19]

Etheredge, III. et al.

[11] Patent Number: 4,983,170

[45] Date of Patent: Jan. 8, 1991

[54] NASOGASTRIC DEVICE

[75] Inventors: Robert W. Etheredge, III., Natick; John C. Charkoudian, Newton, both of Mass.

[73] Assignee: The Kendall Company, Lexington, Mass.

[21] Appl. No.: 173,486

[22] Filed: Mar. 25, 1988

[51] Int. Cl.[5] .............................................. A61M 31/00

[52] U.S. Cl. ...................................... 604/270; 604/280

[58] Field of Search ................................ 604/265-270, 604/264, 280-282; 128/DIG. 22; 428/35-36, 423.1, 424.2; 427/128

[56] References Cited

U.S. PATENT DOCUMENTS

| | | | |
|---|---|---|---|
| 3,975,350 | 8/1976 | Hudgin et al. | 604/57 X |
| 4,631,054 | 12/1986 | Kim | 604/270 X |
| 4,678,660 | 7/1987 | McGary et al. | 604/304 X |
| 4,686,124 | 8/1987 | Onohara et al. | 604/266 X |
| 4,705,709 | 11/1987 | Vaillancourt | 604/265 X |
| 4,735,848 | 4/1988 | Kondo et al. | 427/128 X |
| 4,769,014 | 9/1988 | Russo | 604/270 |
| 4,781,704 | 11/1988 | Potter | 604/270 |

*Primary Examiner*—Max Hindenburg
*Assistant Examiner*—J. P. Lacyk
*Attorney, Agent, or Firm*—Margit Maus; Alvin Isaacs

[57] ABSTRACT

Novel system for providing lubricity to the surface of a nasogastric intubation device, which system comprises a substantially homogeneous mixture consisting essentially of: (1) an effective amount of an unsaturated higher fatty acid having at least 16 carbon atoms; and (2) a polymer compatible therewith.

The mixture may be coated on the surface of the portion of the length of the tube assembly to be lubricated or, alternatively, the acid may be contained in the polymer mix employed in the manufacture of the tube assembly. When the acid-containing surface is contacted with an aqueous alkaline solution prior to intubation, the acid is converted to the corresponding lubricious soap.

20 Claims, 1 Drawing Sheet

NASOGASTRIC DEVICE

BACKGROUND OF THE INVENTION

This invention relates to improvements in nasogastric intubation devices adapted for feeding and/or removal of fluids from the stomach. As is well known, nasogastric devices are commonly employed in postoperative abdominal surgery for emptying the stomach of secretions and gas in order to prevent gastric dilation. They are also used for attaining adequate nutrition; e.g., feeding of high protein liquids, for patients unable to take oral nourishments. Nasogastric intubation may be prescribed, for example, when the normal digestive mechanism is impaired. Impairment may range from localized trauma to the digestive tract to loss of automic function, a common side effect for stroke victims.

Whether intubation be for aspiration or removal of fluids from the stomach or for feeding, intubation is accomplished by inserting the nasogastric tube into a nostril and directing it through the esophagus to the stomach and/or small intestine if the stomach is disfunctional.

In directing the tube, anatomical angulations as well as critical bifurcations of the pathway mandate a semi-rigid object. Misguiding a nasogastric tube into the trachea rather than the esophagus, at the orophargngeal bifurcation can result in respiratory impairment; e.g., pneumothorax or puncturing of the lung. Consequently, some degree of rigidity is needed for proper guidance during intubation.

Paradoxically, however, a rigid intubation device can produce a different category of injuries, namely soft tissue injuries to the delicate mucosal lining as well as to the sinuses, epiglottis, uvula, larynx, etc. Direct impact or friction caused during intubation or removal may cause abrasions and/or hemorrhaging. Laryngitis and difficulty in swallowing are among the most frequent reported post-intubation complications, illustrating the inadequacy of the devices presently used.

It will therefore be seen that a nasogastric tube should be flexible to minimize impact and friction. On the other hand, accurate and safe guidance necessitates a rigid object, which rigidity can cause injury to soft tissues. While the prior art has addressed this paradox, it has not done so successfully.

Generally speaking, two nasogastric intubation procedures are presently dominant. The first method, which seeks to obviate the aforementioned paradox, but is less common, utilizes a flexible tube which is swallowed. This method relies upon a viable and functional swallowing mechanism, impairment of which is a reason for prescribing intubation in the first place. Accordingly, this technique has limited applicability.

The second and generally accepted procedure employs a stylet or wire guide to facilitate intubation. In this form of nasogastric intubation, the stylet is initially housed in the tube and is removed once proper positioning is obtained.

The present invention is directed to the latter device employing a stylet or stiffening wire guide to facilitate proper intubation, and, more particularly, to a novel coating for the stylet to facilitate removal without dislodgement or movement of the tube.

As will be appreciated, a nasogastric tube follows a rather tortuous path from insertion in the nasal passage and then down through the esophagus and eventually into the stomach. Because of the various angulations and the frictional forces resulting therefrom when the stylet contacts the inner wall of the tube during removal, soft tissue injuries will frequently occur.

The prior art has attempted to address this problem by proposing various coating and/or lubricants to decrease friction and thereby lessen the danger of injury. However, none has been entirely satisfactory.

While not intended to be an exhaustive survey of the prior literature pertaining thereto, the following patents are nevertheless considered to be fairly illustrative of the state of the art pertaining to tubes having guide wires intended to be removed once the tube is in place.

U.S. Pat. No. 4,257,921 of Beal proposes the use of Teflon coated wires.

U.S. Pat. No. 4,534,363 issued to Gold teaches using copolymers of methyl siloxane and amino alkyl siloxane.

U.S. Pat. No. 4,589,873 of Schwartz discloses hydrophilic polymers and PVC tubing coated with PVP, polyethylene oxide, polyhydroxyethyl methacrylate, copolymers of PVP with vinyl sulfonic acid or other vinyl acids.

U.S. Pat. No. 4,664,657 of Williamitis teaches using polydimethyl siloxane.

U.S. Pat. No. 4,666,437 of Lambert discloses applying to an article made of vinyl polymers, polyesters or polyacrylates and rubber, a solution of an isocyanate monomer having at least two unreacted isocyanate groups per molecule, an isocyanate prepolymer, or a mixture thereof.

U.S. Pat. No. 4,668,224 issued to Lentz teaches the use of cellulose powder, e.g. acid cellulose.

Finally, British Specification No. 1,600,963 teaches using an interpolymer of PVP and polyurethane.

As previously mentioned, none of the coating or lubricants heretofore suggested have been entirely satisfactory for use with nasogastric tubes.

Accordingly, the task of, this invention, simply stated, is to provide lubricious coating for nasogastric tubes utilized for intubation, which coatings employ readily available and relatively inexpensive materials to provide the requisite lubriciousness for easy removal from the tube.

BRIEF DESCRIPTION OF THE INVENTION

In accordance with the present invention, this task is solved by providing at least the surface of the portion of the tube length assembly to be lubricated with a substantially homogenous mixture consisting essentially of:

(1) an effective amount of an unsaturated higher fatty acid having at least 16 carbon atoms; and (2) a polymer compatible therewith.

The mixture may be present as a coating on the tube assembly surface or, in the preferred embodiment, the acid may be contained in the polymer mix employed in the manufacture of the tube assembly.

While the entire path of the tube length may be so provided with the fatty acid, only the leading end portion of the tube assembly, e.g. the bolus might need be.

In any event, the desired lubriciousness may be obtained simply and efficiently by flushing or otherwise contacting the acid-containing portion with an aqueous alkaline solution to convert the acid to the corresponding soap.

BRIEF DESCRIPTION OF THE DRAWING

The FIGURE is a perspective view of a typical nasogastric tube to which this invention is directed with the stylet partially removed for purposes of illustration.

DETAILED DESCRIPTION OF THE INVENTION

Figure 1:
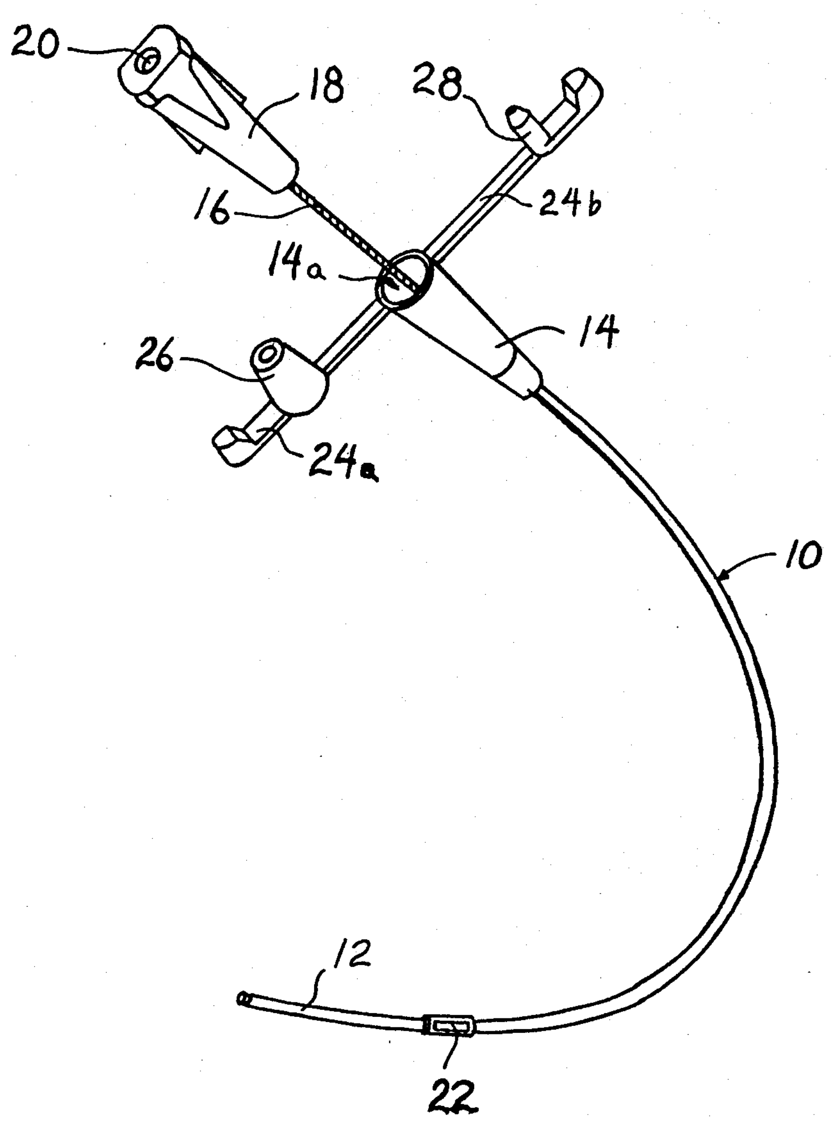

As previously stated, the present invention is directed to reducing the frictional forces encountered in attempting to remove the stylet or stiffening wire from nasogastric tubes following intubation for feeding, aspiration and/or removal of stomach fluids.

Nasogastric devices are of course well known in the medical and surgical arts and a typical device of this description is shown in the illustrative drawing.

As is illustrated therein, nasogastric tube 10, a soft, hollow tubing, has a weighted bolus 12, e.g. a tungsten-weighted bolus, attached to its leading end to help maintain intubation and placement. The opposed or trailing end of tube 10 is secured to hollow cone-shaped tube connector 14. A braided stiffening wire 16 extends from the leading end of tube 10 to where the wire is secured at its trailing end to stylet connector 18 adapted to be removably seated within opening **14*a* of the tube connector. The top or trailing end of stylet connector 18 has a flushing port 20** adapted for applying water to lubricate the stylet, as will be described more fully hereinafter.

At the leading end of tube 10 a pair of opposed openings in the tube wall or "feeding ports" are provided, one of which, 22, is shown in the drawing.

A pair of "ears" or extending flexible bars **24*a* and 24*b* extend on either side of tube connector 14. Ear 24*a* has a hollow cone-shaped member 26 adapted to be removably seated within opening 14*a*, by flexing ear 24*a*, once the stylet and stylet connector are removed. Ear 24*b* has a solid plug 28 adapted to be inserted in the opening in member 26** when the tube is not in use for fluid transmittal.

In operation, just prior to insertion, the stylet is lubricated by flushing the tube through port 20 with water, e.g. 10–15 cc's of water. The bolus tip is then coated with a surgical lubricant, e.g. a lubricating jelly containing phenyl mercuric borate. The tube is then gently inserted into the nostril, aiming down and back toward the ear.

As the bolus drops off back of the soft palate into the pharynx, the patient is encouraged to swallow, if possible. Giving the patient small amounts of water to sip through a straw is sometimes helpful, if not contraindicated.

The practitioner then continues to gently assist the tube passage down the esophagus and into the stomach until the desired position is reached. In doing so, caution must be exercised not to use force. One must proceed slowly and carefully. Slight gagging is normal. However, if the patient coughs or cannot vocalize or shows signs of respiratory distress, this may indicate that the tube has instead entered the trachea. If this occurs, the tube must be withdrawn and inserted into the esophagus.

Before withdrawing the wire stylet, assurance that the tube has reached the desired position is obtained by one or all of the following methods: (a) ausculation, e.g. by injecting with a syringe 10–20 cc of air through tube/stylet assembly and listening for a bubbling sound in the upper left abdominal quadrant; (b) aspiration by using a syringe to withdraw a small amount of gastric contents; or (c) X-ray.

When the tube is properly positioned, slowly and carefully withdraw the stylet from the tube. If resistance is felt, flush the lumen again with water (as described above) and the stylet is then twisted before attempting further withdrawal. [If resistance is still felt, the nurse or other medical assistant is then instructed to stop and consult the physician, thus confirming and reinforcing the previous discussion with respect to the inadequacy of prior stylet lubricating procedures.]

After the stylet is removed, the tube may be closed off with members 26, 28 if desired. The tube is then taped to the patient's nose to stabilize. It is preferably also anchored to the cheek or forehead, avoiding distortion of, or pressure on, the nares.

As seen from the foregoing description of the procedures typically employed by clinicians in hospitals today, the stylet is lubricated by flushing with water through the stylet flushing port and the bolus (leading end of the tube assembly) is coated with a surgical lubricating jelly in a separate coating step. [For convenience, the surgical lubricant is typically contained in a plastic pouch packaged along with the tube.]

In accordance with the present invention, the messy manipulative step of applying the lubricating jelly is eliminated and, more importantly, markedly more efficient lubrication is obtained by fabricating the nasogastric tube assembly so that at least the external surface of the leading end, e.g. the bolus, contains an "effective" amount of an unsaturated higher fatty acid having at least 16 carbon atoms. Upon application of an aqueous alkaline medium prior to insertion, e.g. at bedside, the fatty acid (or ester) is then converted to its corresponding lubricious salt.

As used herein and in the appended claims, the term "effective amount" denotes an amount sufficient to provide the requisite lubriciousness. In general, amounts on the order of about 20 to about 60 percent of the total weight of the polymer-fatty acid mixture are effective for this purpose.

Because of cost and availability, the unsaturated fatty acid employed should preferably be either mono- or di-unsaturated. For the same reasons, oleic and linoleic acid are preferred.

It will of course be appreciated that mixtures of unsaturated fatty acids may be employed in lieu of a single compound in order to provide the effective amount of what may be described as the "lubricious precursor" or "soap precursor" of this invention.

With respect to the fatty acids which may be employed in the practice of this invention, it is to be noted that the saturated analogues are not useful. They are incompatible with the polymeric moiety, e.g. polyurethane. By way of illustration, stearic acid (melting point of 70° C.) creates discontinuities or breaks in the polymer component.

The polymers employed in conjunction with the fatty acid may be selected from those which will form a homogeneous or single phase mixture with the fatty acid and are compatible therewith.

As used herein, "compatible" denotes, in addition to having the physical properties of forming a single phase plasticized mixture with the acid, the property of being chemically innocuous in the sense that it does not adversely react with or affect the ability of the acid to function in its intended way as a lubricious precursor, namely forming a lubricating salt upon application of an alkaline medium.

It will be appreciated that the selected polymer must also be one that is non-deleterious and acceptable for insertion within the body, as intended, nor should it adversely affect the mechanical properties of the tube.

Since nasogastric tubes are typically made of polyurethane, it follows logically that the preferred polymer of this description will be polyurethane, e.g. a medical grade polyurethane such as "Tecoflex" (trademark of Thermedics, Inc.).

Other useful polymers which may be employed in the practice of this invention include, for example, polyvinyl chloride, ethylene vinyl acetate copolymer, polyethylene, polyvinyl pyrolidone, etc.

Where found desirable or expedient to do so, the mixture may contain other reagents performing specific desired functions. For instance, particularly where the mixture is applied as a coating on the surface of a nasogastric tube, it may be desirable to include a detackifying reagent such as stearic or other higher saturated fatty acid to prevent the tube from sticking to itself after the coating step. It is also contemplated that bactericides and the like may be incorporated, although such use is not known to be necessary.

The requisite alkaline medium for forming the lubricious soap may be provided by forming a solution of an alkali such as sodium, potassium or lithium hydroxide at a concentration of pH 8–11, which solution will, upon contact, provide the corresponding alkaline earth metal salt of the fatty acid.

As previously alluded to, it may not be necessary that the entire path of the tube assembly to be inserted be provided with the lubricious surface precursor of this invention, as evidenced by the previous discussion of standard procedure where only the bolus at the leading end is provided with a surgical jelly coating to facilitate insertion. Since a typical bolus such as is shown in the drawing may be on the order of 5.5 cm, it follows a fortiori that at most only this length of the leading end portion of the tube assembly need contain the precursor to achieve beneficial results.

This may be accomplished, for example, by coating the surface of the bolus and/or other tube assembly portion with the precursor mix in accordance with per se known coating techniques, e.g. solution coating, extrusion coating or casting the acid-containing polymer melt on the surface, etc.

It is also contemplated that the portion to be provided with the lubricious precursor may be made from the acid-containing polymer mix itself, in which event the acid will be contained uniformly throughout the thickness of the thus manufactured tube assembly component.

Any advantages in manufacturing the bolus alone in this manner may reside only in any ease or cost reduction which may be derived, as compared with coating the bolus in the manner described above after manufacture. It is theorized, however, that a greater and/or more prolonged lubriciousness may be obtainable in this manner, although no evidence has been observed to substantiate this theoretical possibility.

However, manufacturing the whole or any part of the hollow tube in this manner will provide the added advantage of also providing lubriciousness on the inner surface of the tube, thus facilitating removal of the stiffening wire after insertion.

In other words, instead of flushing water at neutral pH down the stylet port, as described above in connection with the standard procedure used today, an aqueous alkaline solution will be used, allowing the solution to exit through the feeding ports and contact the bolus surface. [To insure proper application, the bolus may, if desired, then be dipped in the alkaline solution before intubation.]

Even where only the bolus or outer surface of the hollow tube contains the novel lubricious precursor of this invention, the invention is well suited for use in conjunction with the invention described and claimed in our concurrently filed copending application Ser. No. (P.F.-1058).

As described and claimed therein, improved lubriciousness of the wire stylet to facilitate removal after intubation is obtained by coating the wire with a mixture consisting of essentially of alkaline earth metal salts of an unsaturated and a saturated fatty acid containing at least 16 carbon atoms.

While the desired lubriciousness may be imparted to the wire in accordance with the invention of the copending application by flushing neutral pH water through the tube, it will be appreciated that an aqueous alkaline solution will be used instead when employed in conjunction with the instant invention.

Thus, while the present invention contemplates that only the outer surface of the leading end portion of the tube assembly need contain the lubricious precursor, it is also contemplated that significant advantages may be derived by manufacturing the tube assembly to be inserted through the nostril from the acid-containing polymer composition so that both the inner and the outer tube surface will contain the lubricious precursor.

The following examples show by way of illustration and not by way of limitation the practice of this invention.

EXAMPLE 1

A 1:1 mixture by weight of oleic acid and "Tecoflex" in tetrahydrofuran (THF) was coated onto the bolus (as shown in FIG. 1) and the THF solvent was then evaporated in ambient air. The resulting lubricious precursor on the bolus was then activated by flushing an aqueous sodium hydroxide solution, pH 10, down the stylet port and allowing it to exit through the feeding ports and wet the surface of the bolus. The increased lubriciousness of the bolus was readily observable by feel.

EXAMPLE 2

Example 1 was repeated except that after coating the bolus and solvent removal, a thin surface coating of stearic acid as detackifier was applied.

EXAMPLE 3

Example 1 was repeated, substituting polyvinyl chloride for the "Tecoflex." Comparable lubriciousness was observed.

To evaluate the efficiency of a lubricious coating of this invention in reducing the coefficient of friction ($\mu$), comparative tests were run wherein that test surface was rubbed first against a polished 304 stainless steel surface and then across a hydrated dermis (pigskin) surface to simulate more accurately the contemplated usage.

These experiments are summarized in the following table.

TABLE 1

| Test # | Test Surface | Control Surface | Lubricant | *μ |
|---|---|---|---|---|
| 1 | Tecoflex | Polished Stainless | dry | 4.2–5.5 |
| 2 | Tecoflex | Polished Stainless | water | 4.2–5.5 |
| 3 | 1:1 Tecoflex/ Oleic Acid | Polished Stainless | water | 4.2–5.5 |
| 4 | 1:1 Tecoflex/ Oleic Acid | Polished Stainless | pH 10 | 0.08 |
| 5 | 1:1 Tecoflex/ Oleic Acid | Hydrated Dermis | water | 2.0 |
| 6 | 1:1 Tecoflex/ Oleic Acid | Hydrated Dermis | pH 10 | 0.04 |

*A coefficient of friction (μ) greater than 1.0 would suggest a strong attraction between the surfaces.

From the first four experiments wherein the control surface was a 304 stainless steel standard test surface, it will be seen that there was no difference in the coefficient of friction whether there was no lubricant (the dry interface of Test 1) or whether water was present at the interface. This was true whether the test surface was Tecoflex (test 2) or a surface containing oleic acid (test 3) in accordance with this invention. However, when an alkaline solution, pH 10 was applied at the interface (test 4), the coefficient of friction was reduced about 98 percent to 0.08.

A corresponding reduction in the coefficient of friction is observed in the two tests run with the hydrated pigskin dermis as the control surface. As is indicated, when ordinary water is used as the lubricant at the interface, the coefficient of friction was 2.0. However, when an alkaline solution, pH 10, was applied at the interface to convert the oleic acid to sodium oleate, again a reduction of about 98 percent to 0.04 was measured.

Since certain changes may be made without departing from the scope of the invention herein described, it is intended that all matter contained in the foregoing description, including the examples, shall be taken as illustrative and not in a limiting sense.

We claim:

1. A nasogastric intubation device including a flexible hollow tubing adapted for insertion through the nose, said device having a leading end portion adapted for positioning in the stomach and a trailing end to remain outside the body and through which stomach fluids may be withdrawn or into which fluid may be fed, at least said leading end portion containing a lubricious precursor composition consisting essentially of a substantially homogeneous mixture of from about 20 to about 60 percent by weight based upon the total weight of said composition of an unsaturated higher fatty acid having at least sixteen carbon atoms and a polymer compatible therewith, said precursor upon contact with an aqueous alkaline medium forming the lubricious salt of said higher fatty acid whereby to lubricate the surface of said portion containing said precursor composition.

2. A device as defined in claim 1 wherein said precursor composition is contained as a coating on the external surface of said device.

3. A device as defined in claim 2 wherein said portion comprises a weighted bolus secured to said hollow tubing.

4. A device as defined in claim 1 wherein said acid is oleic or linoleic acid.

5. A device as defined in claim 4 wherein said polymer is selected from the group consisting of polyurethane, polyvinyl chloride, ethylene vinyl acetate copolymer, polyethylene, and polyvinyl pyrolidone.

6. A device as defined in claim 1 wherein a thin coating of a detackifying agent is provided over said at least portion containing said lubricious precursor composition.

7. A device as defined in claim 1 wherein both the internal and external surfaces of said at least portion contain said lubricious precursor composition.

8. A device as defined in claim 1 wherein said hollow flexible tubing is made from said precursor composition, whereby said acid is substantially uniformly dispersed throughout the thickness of said tubing and is present on both its internal and external surfaces.

9. A device as defined in claim 8 wherein said acid is oleic acid.

10. A device as defined in claim 9 wherein said polymer is polyurethane.

11. In a nasogastric intubation device comprising a soft hollow tubing adjacent leading end for transmittal of fluid through said tubing; a weighted bolus attached to said leading end of said tubing; and a flexible stylet removably insertable in said tubing through a trailing end for guiding placement of said device through the nose and into the stomach;

the improvement wherein the outer surface of said bolus contains an unsaturated higher fatty acid composition, said acid having at least sixteen carbon atoms which upon application of an aqueous alkaline medium will convert said acid to its corresponding lubricious salt, said acid being present from about 20 to about 60 percent by weight based upon the total weight of said outer surface composition.

12. A device as defined in claim 11 wherein said outer surface consists essentially of a homogenous mixture of said acid and a polymer compatible therewith.

13. A device as defined in claim 12 wherein said acid is oleic or linoleic acid.

14. A device as defined in claim 13 wherein said polymer is selected from the group consisting of polyurethane, polyvinyl chloride, ethylene vinyl acetate copolymer, polyethylene and polyvinyl pyrolidone.

15. A device as defined in claim 1 wherein at least the outer surface of said tubing also contains said unsaturated higher fatty acid.

16. A device as defined in claim 11 wherein said hollow tubing is made from a composition consisting essentially of a substantially homogeneous mixture of said acid and a polymer compatible therewith, whereby said acid is substantially uniformly dispersed throughout the thickness of said tubing and is present on both its internal and external surfaces.

17. A device as defined in claim 16 wherein said acid is oleic or linoleic acid.

18. A device as defined in claim 17 wherein said polymer is polyurethane.

19. A device a defined in claim 18 wherein the outer surface of said tubing contains a thin coating of a detackifying agent.

20. A device as defined in claim 19 wherein said detackifying agent is stearic acid.

* * * * *